United States Patent
Maschke

(10) Patent No.: US 8,529,450 B2
(45) Date of Patent: *Sep. 10, 2013

(54) DEVICE FOR PERFORMING A CUTTING-BALLOON INTERVENTION

(75) Inventor: Michael Maschke, Lonerstadt (DE)

(73) Assignee: Siemens Aktiengesellschaft, München (DE)

( * ) Notice: Subject to any disclaimer, the term of this patent is extended or adjusted under 35 U.S.C. 154(b) by 1434 days.

This patent is subject to a terminal disclaimer.

(21) Appl. No.: 11/655,972

(22) Filed: Jan. 19, 2007

(65) Prior Publication Data

US 2007/0173919 A1    Jul. 26, 2007

(30) Foreign Application Priority Data

Jan. 20, 2006  (DE) .................. 10 2006 002 898

(51) Int. Cl.
*A61B 8/00*   (2006.01)

(52) U.S. Cl.
USPC ........... 600/439; 600/407; 600/431; 600/474; 606/159

(58) Field of Classification Search
USPC ............... 60/407–425, 431, 433–471, 474, 60/476, 509; 606/7, 159, 191, 194; 600/407–425, 431, 433–471, 474, 476, 509
See application file for complete search history.

(56) References Cited

U.S. PATENT DOCUMENTS

| | | | |
|---|---|---|---|
| 4,784,636 A * | 11/1988 | Rydell | 604/22 |
| 5,540,959 A | 7/1996 | Wang | |
| 5,827,997 A | 10/1998 | Chung et al. | |
| 6,233,476 B1 | 5/2001 | Strommer et al. | |
| 6,298,261 B1 | 10/2001 | Rex | |
| 6,368,346 B1 * | 4/2002 | Jadhav | 623/1.22 |
| 6,546,271 B1 | 4/2003 | Reisfeld | |
| 6,659,959 B2 * | 12/2003 | Brockway et al. | 600/488 |
| 6,661,240 B1 | 12/2003 | Johnson et al. | |
| 6,765,144 B1 * | 7/2004 | Wang et al. | 174/36 |
| 6,772,001 B2 | 8/2004 | Maschke | |
| 2002/0163994 A1 | 11/2002 | Jones | |
| 2003/0149364 A1 * | 8/2003 | Kapur et al. | 600/439 |
| 2004/0008882 A1 | 1/2004 | Hornegger et al. | |
| 2004/0236416 A1 * | 11/2004 | Falotico | 623/1.42 |
| 2005/0101859 A1 * | 5/2005 | Maschke | 600/427 |
| 2005/0222594 A1 | 10/2005 | Maschke | |
| 2005/0222596 A1 | 10/2005 | Maschke | |

FOREIGN PATENT DOCUMENTS

| | | |
|---|---|---|
| DE | DE 198 52 467 A1 | 7/1999 |
| DE | DE 102 24 011 A1 | 12/2003 |
| DE | 10 2004 015 639 A1 | 10/2005 |
| DE | 10 2004 015 640 A1 | 10/2005 |

(Continued)

OTHER PUBLICATIONS

Biophan Technologies, Inc.; "MRI Shielding for Medical Devices"; Retrieved from Internet on Nov. 7, 2005; Retrieved at www.biolphan.com/shielding.php.

(Continued)

*Primary Examiner* — Tse Chen
*Assistant Examiner* — Mark Remaly

(57) ABSTRACT

The invention relates to a device for performing a cutting-balloon intervention that includes a cutting-balloon catheter with an expandable balloon having axially arranged knives, with the cutting-balloon catheter having a pre-mounted stent.

19 Claims, 4 Drawing Sheets

(56) References Cited

FOREIGN PATENT DOCUMENTS

| | | |
|---|---|---|
| EP | 0 993 804 A1 | 4/2000 |
| EP | 1 034 738 B1 | 9/2000 |
| EP | 1 188 417 A2 | 3/2002 |
| WO | WO 82/04388 A1 | 12/1982 |
| WO | WO 01/11409 A2 | 2/2001 |
| WO | WO 02/078511 A2 | 10/2002 |
| WO | WO 2004/045363 A2 | 6/2004 |
| WO | WO 2004/096097 A2 | 11/2004 |

OTHER PUBLICATIONS

M. Shiba et al.; "New Insight of Cutting Balloon Angioplasty Before Stent Implantation in the Drug-Eluting Stent Era: Serial Volumetric Intravascular Ultrasound Analysis", AS-52; $10_{th}$ Anniversary, Interventional Vascular Therapeutics Angioplasty Summit 2005; Apr. 28-30, 2005 ; pp. 1-43; TCT Asia Pacific, Seoul.

R.J.Dickinson, R.I.Kitney; "Miniature ultrasonic probe construction for minimal access surgery", Physics in Medicine and Biology; 2004 pp. 3527-3538; vol. 49, Institute of Physics Publishing; IOP Publishing Ltd.; United Kingdom.

H. Von Bibra, D. Bone, J-U. Voigt, U. Niklasson, B. Wranne, L. Ryden. ; "Kontrastechokardiographie", Z Kardiol, 2000, pp. I/86-I/96; vol. 89, Suppl. 1.

\* cited by examiner

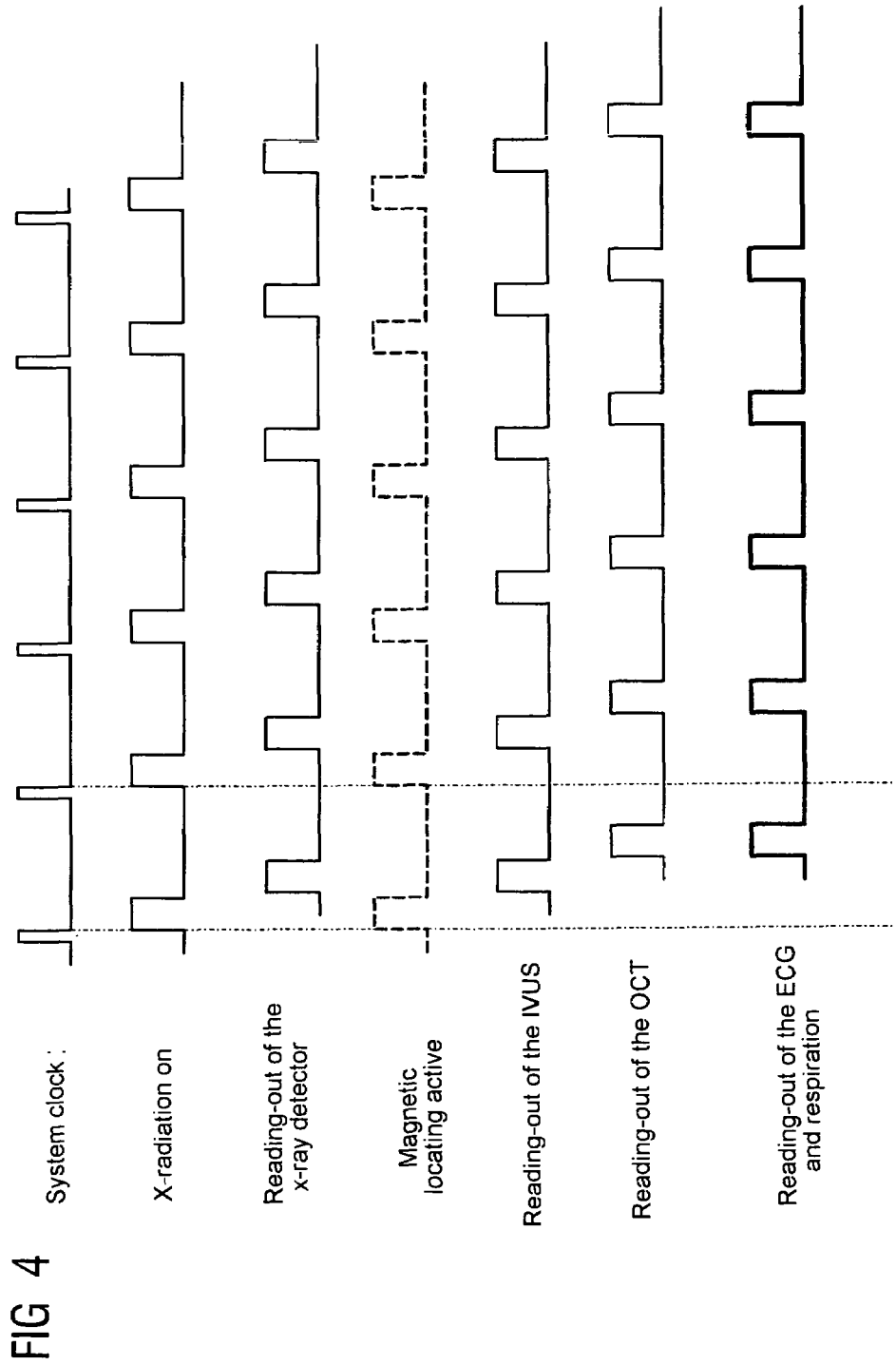

DEVICE FOR PERFORMING A CUTTING-BALLOON INTERVENTION

CROSS REFERENCE TO RELATED APPLICATIONS

This application claims priority of German application No. 10 2006 002 898.8 filed Jan. 20, 2006, which is incorporated by reference herein in its entirety.

FIELD OF THE INVENTION

The invention relates to a device for performing a cutting-balloon intervention that includes a cutting-balloon catheter with an expandable balloon having axially arranged knives. The invention relates further to an associated x-ray apparatus.

BACKGROUND OF THE INVENTION

Vascular diseases are among the commonest disorders having a fatal outcome. Warranting particular mention is myocardial infarction due to diseased coronary vessels. Arteriosclerotic plaque results in more or less severe blocking of the coronary vessels.

Various methods have been developed in recent years for treating such cases of narrowing of, for example, coronary vessels or other parts of the vascular system. Such treatment attempts to clear the plaque away or, as the case may be, destroy it and/or to dilate the vessel in order thereby to remove the vascular occlusion. Interventions of said type for treating a partial or total vascular occlusion are mostly performed under x-ray control using an angiography system, although the vessels concerned such as, for example, the coronary vessels will then be shown only two-dimensionally in silhouette form. To render the vessel clearly visible it is additionally necessary to inject a contrast medium into the vessels, although that will not be able to reach all areas of the vessels in the case of a total occlusion. An associated problem is that many patients are allergic to contrast media or will develop a heat sensation due to the contrast medium. Moreover, patients may also sustain radiation injuries.

For the medical personnel, on the other hand, it is difficult to distinguish between the plaque and vessel wall during the intervention owing to the very limited imaging even when a contrast medium is applied. That increases the risk of clearing away or, as the case may be, destroying tissue at wrong places so that, for example, damage may occur to the vessel wall.

Where attempts have been made to resolve such problems by supplementing x-ray monitoring with additional image monitoring, the problem remains that, depending on the specific type of additional image monitoring employed, it is possible to achieve only a limited spatial resolution or, as the case may be, a good resolution only in the close range, but not a representation that is satisfactory overall.

The cutting balloon is a special balloon bearing three or four small knives depending on its size. These stand up when the balloon opens out and make longitudinal cuts in the vessel's deposits or, as the case may be, "shave" plaque away from the vessel wall before the coronary artery is dilated by the balloon.

The aim of this technique is to reduce or even eliminate the elastic restoring forces in order thereby to achieve a greater diameter of the vessel following dilation. Irregular tears in the vascular endothelium that can be responsible for acute occlusions following ballooning will furthermore be avoided. Studies have shown that hyperplasia (inflammatory reaction with swelling) of the vascular endothelium following balloon dilatation can also be reduced and hence that the restenosing rate can be significantly reduced through using the cutting balloon.

A device functioning on the cutting-balloon principle is described in, for example, WO 82/04388 A1, "Coronary Cutting and Dilating Instrument", and in WO 02/078511 A2, "Inflatable Medical Device with Combination Cutting Elements and Drug Delivery Conduits". What is known as a product is the Cutting Balloon Ultra, for example, made by Boston Scientific, MA, USA; products are also available from Interventional Technologies, San Diego, Calif., USA.

A device for performing a cutting-balloon intervention with OCT monitoring is proposed in U.S. 2005/0222594 A1; a similar device with IVUS monitoring is known from U.S. 2005/0222596 A1.

To keep the vessel open it is often necessary in the treatment of vascular diseases to insert a stent, which is a vessel support that mechanically stabilizes the vessel wall. The use of stents allows the vessel to be further dilated, for example. To insert such stents it has hitherto been necessary first to remove the catheter on which the therapy implement for treating the vasoconstriction is provided then insert the stent using a second catheter. That, though, is a procedure that puts a strain on the patient and entails risks, particularly in terms of restenosing.

SUMMARY OF THE INVENTION

The object of the invention is thus to disclose a relevantly improved device for performing a cutting-balloon intervention.

To achieve said object, a device for performing a cutting-balloon intervention of the type cited in the introduction is provided in the case of which the cutting-balloon catheter has a pre-mounted stent.

The device has a pre-mounted stent serving to support the vessel. Because such a stent—also understood, of course, as meaning a plurality of separate stents serving as a vessel support—is arranged on the cutting-balloon catheter for treating the vascular occlusion, there is no need to remove a catheter again that has been used for clearing the plaque, for instance. The stent can be inserted by means of the cutting-balloon catheter simultaneously with the therapy implements. A significantly reduced risk of restenosing ensues therefrom.

The stent can be pre-mounted in the vicinity of the catheter's tip. The device for supporting the vessel will thus from the outset be located in the area undergoing therapy so that the stent can then, without moving the catheter significantly, be positioned at the right place where the therapy was performed.

A second expandable balloon can furthermore be provided in the vicinity of the catheter's tip, with the pre-mounted stent being able to be positioned and/or secured in position as a function of said second balloon being expanded. The stent will thus be pressed into the vessel wall, for example, when the balloon is filled and thereby secured in position. The stent can in the unopened-out condition be located on the balloon or, as the case may be, in the vicinity thereof so that the stent's location relative to the vessel will be influenced when the balloon is expanded. For example, when the balloon is inflated the stent can be deformed beyond its elastic limits or, as the case may be, overstretched so that the shape resulting from the balloon being inflated will afterwards be retained. With the aid of the balloon, the stent will consequently be selectively deformed and positioned or, as the case may be, secured in position or anchored in the area of the vessel.

The stent can also be embodied as being at least partially self-opening-out. In this case a cladding, for example, made of a plastic material and at least partially surrounding the stent will be removed, whereupon the relevant area of the stent will open out. As a rule, either a stent opening out with the aid of a balloon or a self-opening-out stent is used. It is, though, also conceivable for both these possibilities for inserting the stent or, as the case may be, securing it in position in the area of the vessel to be combined.

The stent can, moreover, be embodied at least partially from metal, in particular high-grade steel or nitinol. Lattice-type or mesh-type arrangements consisting of, for example, steel or a specific metal or other metal alloys, for example the nickel-titanium alloy nitinol or another shape-memory alloy, are as a rule used for stents.

The stent can also be embodied at least partially from bioresorbable material, in particular biological material and/or magnesium and/or bio-engineering material and/or plastic. For example polymers can be used. Bioresorbable materials have the advantage of disintegrating after a certain, possibly predefined period of time so that, when no longer necessary as a vessel support after a certain period of time, the stent will degrade automatically and so be removed, with no further intervention and posing no risk for the patient. Other advantageous materials and combinations of materials can, of course, also be used for the stent that impact positively on the vessel's inner surface or, as the case may be, can support the vessel and maintain its open condition. Furthermore, requirements have to be adhered to regarding the possibilities for insertion as well as for visualizing for medical examinations, for instance. Alongside this, the stent materials' properties have to be taken into account in terms of their effect on blood flow or blood clotting.

The stent is advantageously embodied as being coated, in particular with a nano coating and/or active-component coating. Coatings of said type make it possible to improve, for example, guiding of the cutting-balloon catheter on which the stent or stents is/are pre-mounted. A coating containing active components or medicaments that will be released over a certain period of time or at a specific time is used, for example, in order to control the division of the vessel wall's cells. Moreover, the risk of restenosing can be further reduced by way of appropriate active components or medicaments that are released once the stent has been positioned in the area of the vessel. Instances of active components or medicaments of said type are Sirolimus, Paclitaxel, Everalimus, Rapamycin, and FK 506.

The cutting-balloon catheter can furthermore have an integrated unit for image monitoring. The cutting-balloon catheter can in particular be embodied as an integrated unit with an OCT sensor and/or IVUS sensor. The cutting-balloon catheter can furthermore be embodied having a position-sensor system.

The abbreviation OCT stands for "Optical Coherence Tomography", the basic principles of which are based on the Michelson interferometer. Image data offering a very good spatial resolution particularly in the close range can be recorded with OCT sensors.

When a sensor of such kind integrated in a catheter is inserted into the vessel separately, there is the problem that each time the vascular occlusion is further treated with the cutting-balloon catheter the separate OCT catheter first has to be withdrawn from the vessel again in order then to insert the cutting-balloon catheter.

That is avoided by means of the inventive device for performing a cutting-balloon intervention in the case of which the OCT sensor is embodied with the cutting-balloon catheter in an integrated unit.

Alongside this, the integrated unit may have an IVUS sensor that is based on intravascular ultrasound technology and with which additional image data can likewise be obtained. It is thus possible not only to image the state of the lumen of vessels but also to produce an image of the vessel walls. The ultrasound method alone, though, offers only a limited spatial resolution. If an IVUS sensor is embodied as a constituent part of a separate catheter, then said catheter will, similarly to the OCT catheter, have to be additionally inserted into the vessel then removed therefrom again prior to insertion of the cutting-balloon catheter, as a result of which the therapy will be made more difficult and additional strains placed on the patient. That is avoided by an inventive integrated solution.

With the inventive device for performing a cutting-balloon intervention, both these possibilities of imaging by means of a OCT sensor and IVUS sensor are, where applicable, integrated in the device for performing a cutting-balloon intervention so that a cutting-balloon catheter is embodied for performing therapy and for image monitoring. A position-sensor system is expediently also provided that enables the catheter to be precisely located in the patient's body. Previous partial or separate solutions are thus replaced by an integrated combination allowing optimal diagnostic imaging and minimally invasive medical treatment. Thanks to the cutting-balloon catheter the device is able to disperse the vascular occlusion and, thanks to the different OCT and IVUS imaging techniques, able at the same time to make the catheter clearly visible in relation to the vessel, for which purpose the position-sensor system is employed additionally for locating the device in order thereby to produce recordings near to and further from the vascular occlusion that exhibit a high spatial resolution.

The image information of the OCT and IVUS recordings can therein be mutually combined for example for producing superimposed images, with it further being possible to produce combinations with data of a conventional x-ray monitoring means or suchlike. Two-dimensional or, in particular, also three-dimensional recordings can thus be obtained that exhibit a high diagnostic quality, with intermediate removal of one or both separate imaging catheters and re-insertion of the cutting-balloon catheter being eliminated thanks to the device's embodiment as an integrated catheter, as are the attendant disadvantages for the patient and for the doctor performing the therapy. Combining the two OCT and IVUS imaging techniques with a cutting-balloon catheter thus allows vascular occlusions to be optimally treated using image monitoring during which detailed image information is obtained across all imaging ranges, both near and far.

The OCT and IVUS sensor each have signal leads leading to the catheter's tip on which are provided the sensors for the optical coherence tomography or, as the case may be, the intravascular ultrasound process. The OCT sensor can therein be embodied as a pivoting mirror on which are reflected the emitted light signals for detecting interferences.

In all, therefore, therapy is made possible using a single catheter with which both the vascular occlusion can be removed, where applicable accompanied by appropriate image monitoring, and a stent maintaining the vessel's open condition can be inserted therein. The therapy will thus require fewer procedural steps, with there also being the possibility, given the appropriate embodiment, of monitoring the process by means of three-dimensional recordings. Representation of the near area can be insured when OCT and IVUS have been combined, while adequate images of deeper tissue layers will be obtained at the same time. Utilizing the signals of a position-sensor system will allow the location and motion of the integrated therapy catheter to be imaged with the aid of the IVUS signals, OCT signals, and cited—for instance electromagnetic—signals of the position-sensor system so that the x-radiation to which the patient is exposed can be reduced.

The device can furthermore be embodied having an automatic advancing and/or withdrawing device. That will enable the cutting-balloon catheter to be inserted into or, as the case may be, withdrawn from the vessels at a defined speed, as a result of which for example complications due to overhasty or imprecise manual guiding can be avoided.

The OCT and/or IVUS catheter's signal leads can be ducted inside a catheter cover of the cutting-balloon catheter for treating the vascular occlusion, in particular inside a hollow drive shaft for the OCT and/or IVUS sensor. The cutting-balloon catheter can therein be embodied as a tubular catheter with a catheter cover having at least one or more lumina. The signal leads for OCT and IVUS imaging that connect the OCT and IVUS sensors on the catheter device's tip to a signal and/or drive unit are where applicable ducted in lumina in said catheter cover of the cutting-balloon catheter, which in view of its function has a rather larger diameter. There is expediently a common drive shaft or separate drive shafts for the OCT and IVUS sensor to enable, where applicable, independent driving of the two sensors. The respective signal leads are expediently ducted in a protected manner in a drive shaft of said type embodied having a cavity.

The OCT sensor and/or IVUS sensor and/or a surrounding drive shaft can be embodied as rotatable. If instead of an outer drive shaft only the IVUS sensor or, as the case may be, OCT sensor, connected in each case to their signal leads, is rotated, then there will be no friction between the catheter device and the vessel's internal wall. For example an image sensor, embodied as a mirror, for the OCT is turned through rotating of the IVUS catheter or, as the case may be, OCT catheter. Instead of an external drive shaft there can, of course, also be a likewise rotatable drive shaft inside an outer catheter cover.

The OCT and/or IVUS catheter's image sensor can be located in front of or behind the expandable balloon having axially arranged knives. Depending on the specific type of arrangement, images can be produced showing the effect of the cutting-balloon intervention. Thus different information can be obtained relating to a further course of therapy or, as the case may be, to an assessment of therapy just performed or still in progress.

The catheter device can have at least one transparent exiting area for the IVUS sensor's ultrasound and/or the OCT sensor's light. Thus, for example, a surrounding catheter cover of the device can have one or more transparent exiting windows in the vicinity of its tip that allow infrared light or, as the case may be, ultrasound to pass through and thus enable imaging. It is, of course, also conceivable for a transparent embodiment to be provided overall or, as the case may be, not just in the vicinity of the tip of the catheter device.

The catheter device can, for three-dimensional imaging, be embodied for rotating and simultaneously withdrawing and/or advancing the OCT sensor and/or IVUS sensor. Through rotating and simultaneous withdrawing or, as the case may be, advancing both image sensors or one of them, it is possible to produce three-dimensional recordings using the cutting-balloon catheter, with it being conceivable for both image sensors to rotate and simultaneously be moved in a longitudinal direction, which is to say, for example, forward in each case.

The position-sensor system can inventively be embodied as being electromagnetic or ultrasound-based. Position sensors on the catheter's tip make it possible to obtain a precise three-dimensional representation of the vessel because motion artifacts due to the catheter's dimensions relative to the vessel can be avoided. The vessel's center line and, where applicable, envelope curve is for this purpose approximated by applying suitable mathematical methods and the relevant information combined with the sensor positions. That makes a precise three-dimensional reconstruction possible that has been corrected for displacements.

From the initially two-dimensional OCT recordings or, as the case may be, IVUS recordings it is possible with the aid of electromagnetic position sensors to produce three-dimensional recordings that enable the therapy to be assessed much better. The electromagnetic transmitters or the receivers, also, can be in part located in the catheter, which in turn results in the corresponding arrangement of the transmitters or, as the case may be, receivers outside the body. Usually at least one transmitter is assigned to a receiver, or vice versa, for spatial locating, with, in certain circumstances, a combination of two transmitter devices with one receiver, or vice versa, also being possible, for example when angular relationships are known. If the coils of an electromagnetic positioning system are not arranged exclusively mutually orthogonally but at any angle, for example an angle of 60°, the corresponding coil unit can be made smaller so that arranging in the catheter will be rendered unproblematic.

The position sensors are expediently located in the vicinity of the cutting-balloon catheter's tip. That will allow locating in the area that is also particularly of interest for the therapy being performed and hence for imaging by means of the OCT technique or, as the case may be, IVUS technique. Following the installation of an investigation device with an inventive cutting-balloon catheter having a position-sensor system, calibrating will advantageously be performed and magnetic field curves stored for guidance.

The cutting-balloon catheter can be embodied for automatic mechanical navigation and/or for magnetic navigation. Automatic mechanical navigation will allow computed movements to be reliably and stably executed using robotics. Magnetic navigating of the combined catheter is likewise also possible, with the cutting-balloon catheter provided with magnets then being controlled and driven by an external magnetic field. That can be done using permanent magnets or, as the case may be, electromagnets.

At least one physiological sensor can also be provided on the cutting-balloon catheter's tip. Via microsensors or nanosensors it will then be possible to perform a temperature measurement or pressure measurement or, as the case may be, determine a ph value and suchlike. Additional information will hence be obtained that can help decide on the further course of a therapy or, as the case may be, will indicate whether the therapy is proceeding without complications.

The cutting-balloon catheter can have a coating for screening the device and/or better ducting it in the vessel. Magnetic interference fields that may disturb the recorded signals can be shielded using a screening means. One possibility for providing screening of said type is offered by a thin-film layer consisting of conductive nano particles. Thermal isolation may also be necessary for protecting the electronic components and sensors from a cooling medium. Via an appropriate coating provided on the combination catheter it is possible to reduce the frictional resistance while the catheter is being guided or, as the case may be, ducted through the vessels. A silicon coating can be used for this or, as the case may be, a coating employing materials based on nanotechnology.

An image sensor of the OCT catheter can be located in the catheter device's longitudinal direction in front of or behind an image sensor of the IVUS catheter. That means that initially the OCT sensor in front of which the IVUS sensor is arranged can be located on the catheter device's tip, in the direction, therefore, of the therapy being performed. The sensors can, however, alternatively also be arranged in reverse sequence. The only crucial factor is how optimal image monitoring can be achieved in the respective case.

The cutting-balloon catheter can moreover have a lumen, in particular a separate lumen, which is embodied for injecting an ultrasound contrast medium. Via a lumen that is present in any event or via an additional lumen it is thus possible to inject an ultrasound contrast medium in order thereby to further improve the IVUS sensor's imaging.

The invention further relates to an x-ray apparatus that has a device with a cutting-balloon catheter of the type described.

The x-ray apparatus of said type thus has a radiation source that is linked to a corresponding system control and produces x-rays with which a patient located on a corresponding positioning apparatus is irradiated and which are detected by means of a detector. The x-ray images produced can be combined via a data bus with the image data and other data recorded by the catheter device that was inserted into the patient's body and has the OCT sensor and IVUS sensor or, as the case may be, correlated for evaluation purposes. The results of image processing can be shown to the doctor performing the treatment on a display unit of the x-ray apparatus. The therapy being performed on the vascular occlusion such as, for instance, the removal of plaque or, as the case may be, opening out of the stent can thus be tracked with optimal image monitoring, where applicable throughout the treatment.

The x-ray apparatus can for this purpose be embodied for combining and/or overlaying the OCT data and/or IVUS data with x-ray data and/or image data obtained using other modalities. The following modalities are possible for overlaying: Radiography (fluoroscopy), angiography, discrete tomography, positron-emission tomography, nuclear medical diagnostics (PET/SPECT), computer-assisted tomography, nuclear magnetic resonance tomography including intracardial MR, optical recordings including endoscopy, fluorescence, and optical markers.

The generated images of the cutting-balloon catheter can be displayed by means of a common user interface together with the x-ray images and will thus be easy to see for the user at a single defined location so that fast and better diagnosing and therapy will be possible. There are hitherto unknown diagnostic and therapy-related advantages thanks to all kinds of possibilities for superimposing two-dimensional and two-dimensional or two-dimensional and three-dimensional images, extending to four-dimensional recordings of the angiographic x-ray images and images of the cutting-balloon catheter for segmenting, registering, and image merging. The images can be overlaid with images obtained using other modalities such as sonography, fluoroscopy, nuclear magnetic resonance tomography and suchlike in advance of treating the vascular occlusion or, as the case may be, which were produced in parallel in a hybrid system, which is to say in a combined system including the x-ray apparatus.

The x-ray apparatus can inventively have at least one image-correcting unit embodied for correcting image artifacts due to the stent. What is expediently used for this is an image-correcting unit that is present in any event, which is to say, for example, a correcting processor of the image-processing devices for IVUS imaging, OCT imaging, and x-ray imaging or, as the case may be, for processing the sensor signals. Image correcting is therein based on the fact that the structure of the inserted stent or, as the case may be, stents is known so that it/they can be taken into account during image reconstruction. Image artifacts or, as the case may be, disruptions in the image presentation can thus be selectively computed out.

The invention relates further to a method for image monitoring while therapy is being performed on a partial and/or total vascular occlusion by means of a device with a cutting-balloon catheter that has an expandable balloon with axially arranged knives for treating the vascular occlusion and which is embodied as an integrated unit having a pre-mounted stent and an OCT catheter and/or IVUS catheter and/or a position-sensor system for image monitoring. With said method, image monitoring is carried out in the course of therapy performed on a vascular occlusion during which a device as described in the foregoing is used. The cutting-balloon catheter is for this purpose first inserted under x-ray control, for instance, and, where applicable, with supplementary contrast medium being injected and, for example, angiographic plain recordings are produced. Where applicable, the recordings of the electromagnetic position sensors or, as the case may be, another position system are then produced. Said recordings can be overlaid with the plain angiography recordings, and the cutting-balloon catheter is navigated to its target position in the vessel based on the recordings. These steps can in part be performed in parallel and automatically with no user intervention.

When a desired target position has been reached, where applicable a rinsing fluid for optical coherence tomography can be injected and the vessel's occlusion viewed two-dimensionally or three-dimensionally with high resolution using OCT and IVUS recordings. A three-dimensional reconstruction can be made with the aid of electromagnetic position sensors, followed by overlaying with the plain angiography recordings. The therapy unit, which is to say the cutting-balloon catheter, is positioned in the vessel at the location scheduled for treatment and the positioning checked using the OCT and IVUS image data. The vascular occlusion is then opened or, as the case may be, cleared, with the procedure being repeated until the plaque has been cleared away on all sides along the corresponding length. Finally, the opened occlusion can be evaluated after another check using image monitoring. The vessel opening is kept open with the stent, which is for this purpose opened out from its pre-mounted position and positioned in the vessel by, for example, expanding a balloon provided for the purpose. The cutting-balloon catheter can be removed following successful therapy and positioning of the stent.

Alongside this, the method can be applied not only to coronary vessels but also to vessel-like cavities in general, for example organ cavities, in the bodies of humans or animals.

The therapy can thus be performed with fewer procedural steps, omitting, for example, removing and re-inserting imaging catheters or, as the case may be, separate catheters bearing stents. Moreover, only the combination catheter is necessary for performing the therapy, so in the final analysis just a single catheter compared to the separate catheters used hitherto. Good recordings in the near range can be produced using OCT imaging, while the IVUS sensor enables good imaging in the surrounding tissue layers. Three-dimensional recordings can be reconstructed with the aid of the position-sensor system and, where applicable, the doses of x-radiation applied can be reduced. As well as additional information being supplied about the occlusion and plaque, the correct positioning, in particular of the therapy unit, can be better checked.

BRIEF DESCRIPTION OF THE DRAWINGS

Further advantages and specifics of the invention will emerge aided by the following exemplary embodiments and from the drawings.

FIG. 4 is a schematic of the sensor readout produced during implementing of the inventive method with the x-ray apparatus shown in FIG. 3.

DETAILED DESCRIPTION OF THE INVENTION

Figure 1:
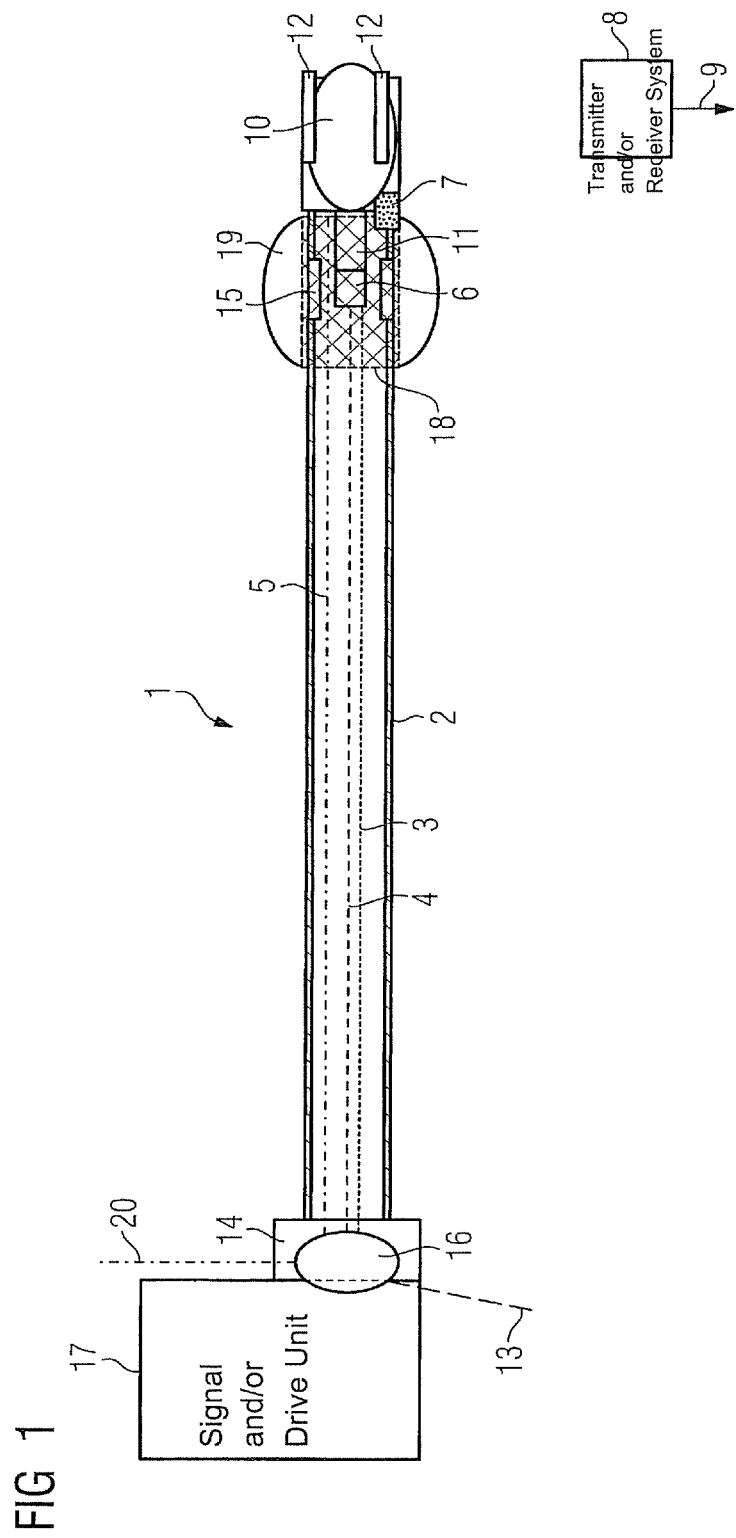
FIG. 1 shows a first exemplary embodiment of an inventive device with a cutting-balloon catheter.

FIG. 1 shows an inventive device 1 with a cutting-balloon catheter. The inventive device 1 has a hollow flexible drive shaft 2 in which are integrated an OCT signal lead 3 and an IVUS signal lead 4. The OCT signal lead 3 is therein embodied as a glass-fiber lead. Further located in the flexible drive shaft 2 is a signal lead 5 of the position-sensor system embodied as an electromagnetic sensor system. Thus what results through the surrounding drive shaft 2 is an integrated unit that replaces the separate catheter used hitherto in favor of better image monitoring and treating of vascular occlusions.

What is to be preferred is an embodiment, not shown here, in which it is not the drive shaft 2 that rotates but only the IVUS and OCT sensor in order thereby, where applicable, to avoid friction between the catheter device and the vessel's interior wall and simultaneously cause the OCT sensor to turn.

The signal lead 5 of the electromagnetic position-sensor system leads to antennas 7, which are located on the tip of the device 1 and arranged in the x, y, and z direction. They are shown here only schematically. The antennas 7 interact with a transmitter and/or receiver system 8 that is located outside the body and in turn has position sensors or, as the case may be, detectors. The data, as indicated by the arrow 9, is forwarded from there to a position-detecting unit via a corresponding interface.

Located on the tip of the cutting-balloon catheter is an expandable balloon 10 that can be filled with a dilating medium such as air, nitrogen, sodium chloride solution (NaCl), or $CO_2$ via a line 20. The balloon has a plurality of axially arranged knives 12 with which blockages in vessels can be cleared.

An OCT sensor 6 connected to the OCT signal lead 3 is embodied as a pivoting mirror, with said OCT sensor 6, like the IVUS sensor 11, being located next to the balloon 10. Provided in the vicinity of the OCT sensor 6 or, as the case may be, IVUS sensor 11, is a transparent exiting window 15 of the surrounding drive shaft 2, through which window the infrared light and ultrasound can exit to enable imaging. The OCT sensor can in an alternative embodiment not shown here be embodied as a turning shaft on which is provided a light-exiting or, as the case may be, light-entering window.

Provided also at the rear area of the device 1 is a terminal 13 for injecting contrast medium and/or rinsing fluid. Operating of the device 1 is enabled by way of a mechanical connecting system 14 and a rotation coupling 16 for the terminals. The device 1 can be advanced and withdrawn therewith, with a rotation motion of, for example, the OCT sensor being able to take place simultaneously. The catheter can be advanced or, as the case may be, withdrawn by means of an automatic advancing and withdrawing device or manually. Finally, a signal and/or drive unit 17 serving to produce the motion as well as to generate and record signals is connected downstream.

The catheter device 1 moreover has a pre-mounted stent 18 which is embodied as a metal-wire mesh and in FIG. 1 has been sketched in its non-expanded position. In alternative embodiments the stent can also consist of other materials such as bioresorbable materials. On completion of therapy performed with the aid of the balloon 10 of the cutting-balloon catheter, the stent 18 will be expanded by means of a second expandable balloon 19, whose feeders have not been shown here in the interest of greater clarity. The balloon 19 is filled so that the stent arranged thereon will be expanded in the direction of the vessel wall and pressed into it. The positioning of the stent 18 is monitored with the aid of the imaging sensors.

The inventive combination catheter thus allows a cutting-balloon intervention to be performed on a vascular occlusion accompanied by optimal image monitoring by OCT and IVUS in combination with electromagnetic position sensors, and a stent to be positioned in the vessel.

Figure 2:
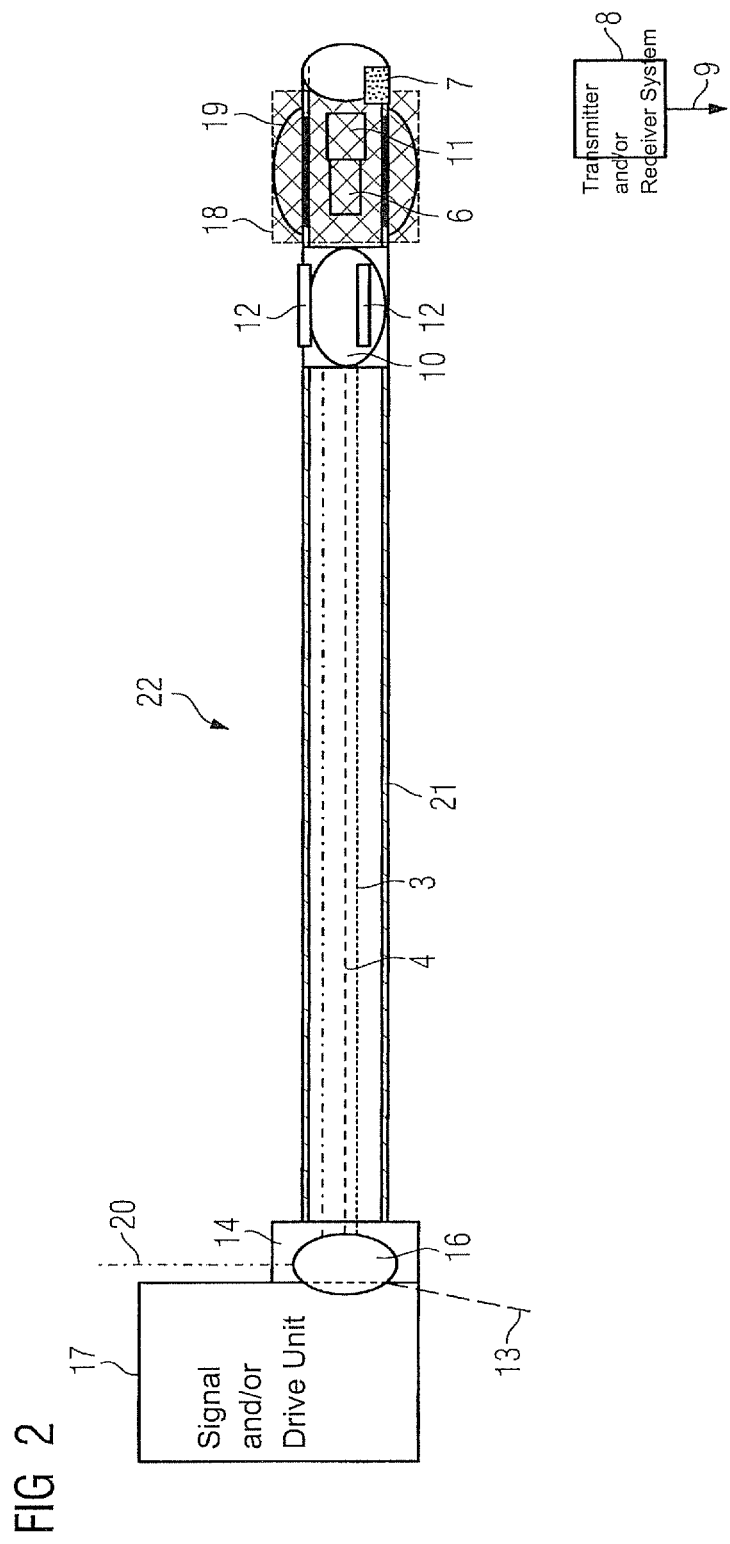
FIG. 2 shows a second exemplary embodiment of an inventive device with a cutting-balloon catheter.

FIG. 2 shows a second exemplary embodiment of an inventive device with a cutting-balloon catheter, with the same reference numerals being used for identical components.

As a departure from the first exemplary embodiment, located on the tip of the device 22 with the cutting-balloon catheter is the expandable balloon 19 for expanding a stent. Provided there alongside a tubular catheter cover 21 is, inside this, a hollow flexible drive shaft in which are integrated an OCT signal lead 3 and an IVUS signal lead 4. The signal lead 3 or, as the case may be, 4 leads to an OCT sensor 6 embodied as a mirror and to an IVUS sensor 11 located in front of it in the direction of the therapy being performed. It is alternatively also possible to use a turning glass fiber having reflective surfaces. The catheter cover 21 has on its end a transparent circular window through which the light or, as the case may be, ultrasound of the OCT sensor 6 and IVUS sensor 11 can exit.

When the vascular occlusion has been cleared, the pre-mounted stent 18 will be opened out as a function of the filling of the balloon 19 and positioned in the vessel to support it. The stent 18 is provided with a medicament coating via which a defined amount of a medicament is released to prevent restenosing. Other exemplary embodiments are, of course, conceivable where the stent does not have a medicament coating. The structure of the stent 18 being known, imaging while therapy is in progress will not be adversely affected thereby.

Figure 3:
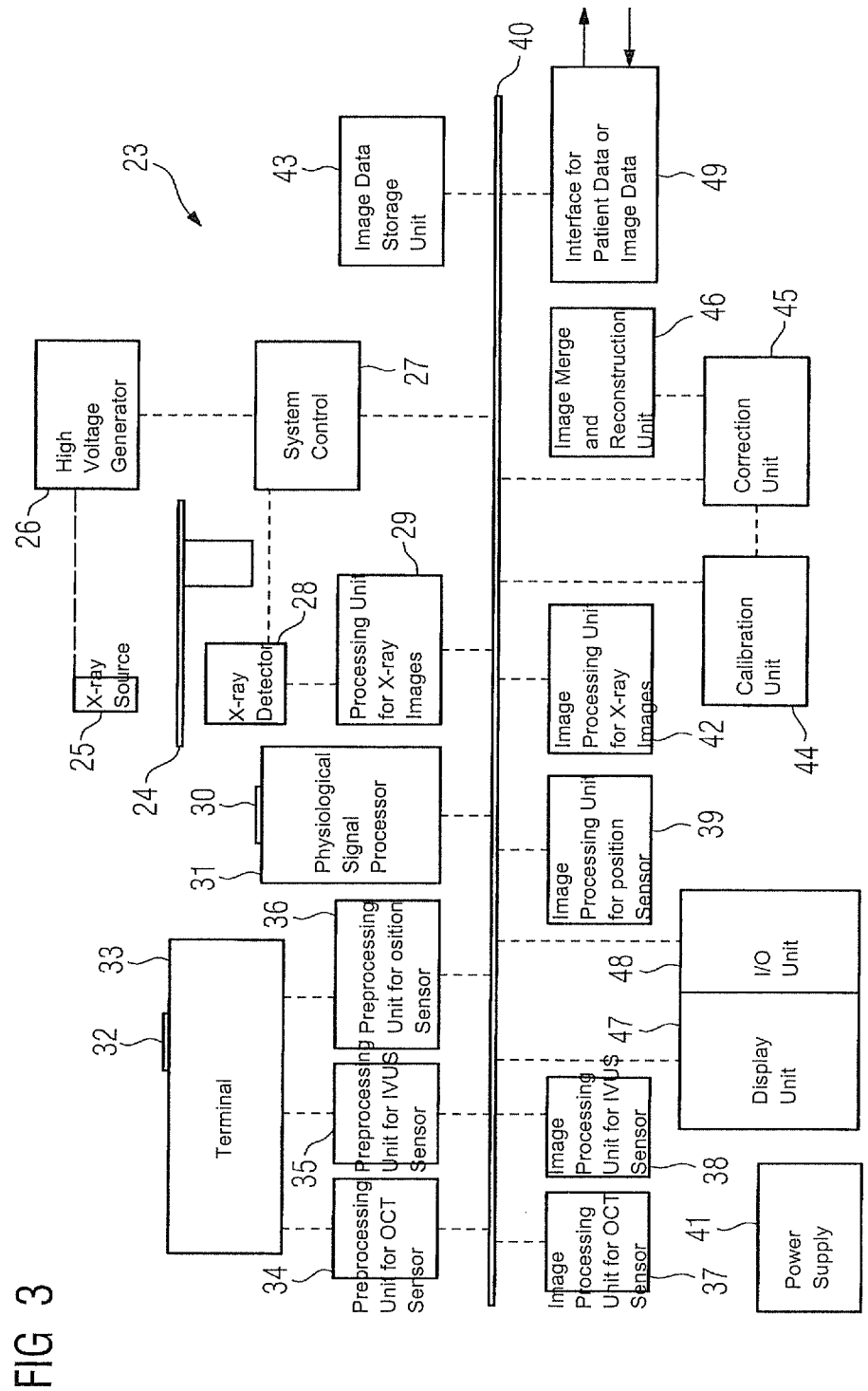
FIG. 3 shows an inventive x-ray apparatus with a cutting-balloon catheter.

FIG. 3 shows an inventive x-ray apparatus 23 with a device having a cutting-balloon catheter, which x-ray apparatus is based on emitting high-frequency radiation. For the therapy, a patient who is not shown here is made to lie on an operating table 24 and radiation is emitted from a radiation source 25 in the direction of the operating table 24. The radiation is produced by means of a high-voltage generator 26 controlled via a system control 27. Arranged opposite the radiation source 25 is an x-ray detector 28, in turn connected to a pre-processing unit 29 for x-ray images. Provided in addition is a terminal 30 for physiological sensors that is coupled to a physiological signal processor 31 for measuring ECG signals or pulse signals or, as the case may be, a patient's breathing and blood pressure.

The therapy itself is performed, accompanied by image monitoring using OCT, IVUS, and the electromagnetic position-sensor system, via a terminal 32 for the cutting-balloon catheter with a connection being made to a signal interface 33. Provided in addition are in each case pre-processing units 34 to 36 for the OCT recordings, the IVUS recordings, and the electromagnetic position-sensor system. The associated image-processing units 37, 38, and 39 are connected to the data bus 40. Power is supplied via a power-supply unit 41. An image-processing unit 42 for the x-ray images is furthermore connected to the data bus 40, which additionally has a connection to an image-data memory 43 for filing and storing the recorded images. A calibration unit 44 as well as an image-correcting unit 45 enable interference fields or, as the case may be, artifacts in the imaging to be taken into account. The image-correcting unit 45 has, inter alia, a correction processor for eliminating image artifacts due to a stent requiring to be inserted or, as the case may be, that has been inserted and mounted in position. The stent's known structure is used for this. Image merging and reconstructing take place in an image-merging and/or reconstruction unit 46. Provided in addition is an interface 49 to a patient-data and image-data system.

The image data obtained from OCT, IVUS, and the position-sensor system as well as the x-ray images and possible merged images obtained using the various image-recording techniques are presented two-dimensionally, three-dimensionally, or four-dimensionally on a display unit 47. The display unit 47 is connected to an input unit 48 for user inputs. The subsystems and components according to FIG. 3 are advantageously integrated into a single device.

FIG. 4 is a schematic of the sensor readout produced during implementing of the inventive method with the x-ray apparatus 23 shown in FIG. 3. The sensors of the x-ray apparatus 23 are read out partially in time-lagged and clocked fashion. A system clock is first defined in which individual system pulses are generated, with the x-radiation being switched on and magnetic locating being activated following on from said pulse generating. The x-ray detector will be read out after the x-radiation has been switched off and the IVUS data read out simultaneously. The OCT data will then be read out, that taking place simultaneously with reading-out of the ECG and the data relating to respiration. The individual sensors will thus be read out or, as the case may be, the components of the device with the cutting-balloon catheter thus controlled in such a way that mutual interference can be precluded. The time-lagged and clocked manner of reading-out shown here is herein to be regarded as exemplifying reading-out with interference being avoided.

The invention claimed is:

1. A device for performing a cutting-balloon intervention on a patient, comprising:
   a cutting-balloon catheter with an expandable balloon comprising an axially arranged knive;
   a stent that is pre-mounted to the cutting-balloon catheter on a second expandable balloon; and
   an integrated unit comprising an OCT sensor and an IVUS sensor located next to the expandable balloon for image monitoring;
   a drive unit that advances or withdraws the cutting-balloon catheter and simultaneously rotating the OCT sensor and the IVUS sensor;
   an OCT signal lead and an IVUS signal lead that connect the OCT sensor and the IVUS sensor to the drive unit respectively for rotating the OCT sensor and the IVUS sensor; and
   a flexible drive shaft in which are the OCT signal lead and the IVUS signal lead,
   wherein the flexible drive shaft does not rotate and only the OCT sensor and the IVUS sensor rotate to avoid a friction between the cutting-balloon catheter and a vessel wall of the patient.

2. The device as claimed in claim 1, wherein the expandable balloon is located on a tip of the cutting-balloon catheter and the second expandable balloon comprising the stent is located behind the expandable balloon.

3. The device as claimed in claim 1, wherein the stent is at least partially self-opening out.

4. The device as claimed in claim 1,
   wherein a material of the stent is at least partially a metal, and
   wherein the metal is selected from a group consisting of: high grade steel, nitinol, and shape memory alloy.

5. The device as claimed in claim 1,
   wherein a material of the stent is at least partially a bioresorbable material, and
   wherein the bioresorbable material is selected from the group consisting of: biologic material, magnesium, bio-engineering material, and plastic.

6. The device as claimed in claim 1,
   wherein the stent comprises a coating for guiding the cutting-balloon catheter, and
   wherein the coating is a nano coating or an active component coating.

7. The device as claimed in claim 1,
   wherein the cutting-balloon catheter comprises a position sensor system, and
   wherein the position sensor system is an electromagnetic sensor system.

8. The device as claimed in claim 1, wherein the cutting-balloon catheter comprises a device for pushing or pulling the cutting-balloon catheter.

9. The device as claimed in claim 1, wherein a physiological sensor is arranged on a tip of the cutting-balloon catheter.

10. The device as claimed in claim 1, wherein the cutting-balloon catheter comprises a coating for screening or reducing a frictional resistance in a vessel of the patient.

11. The device as claimed in claim 1,
    wherein the cutting-balloon catheter comprises a lumen for injecting a contrast medium, and
    wherein the contrast medium is an ultrasound contrast medium.

12. The device as claimed in claim 1, wherein the stent comprises an active component selected from the group consisting of: Sirolimus, Paclitaxel, Everolimus, Rapamycin, and FK 506.

13. The device as claimed in claim 1, wherein the second expandable balloon comprising the stent is located on a tip of the cutting-balloon catheter and the expandable balloon is located behind the second expandable balloon.

14. An x-ray apparatus for performing a cutting-balloon intervention on a patient, comprising:
    a radiation source that emits radiation to the patient;
    a radiation detector that records an x-ray image data of the patient by detecting the radiation emitted from the radiation source;
    a cutting-balloon catheter with an expandable balloon comprising an axially arranged knive that performs the cutting-balloon intervention;
    a stent that is pre-mounted to the cutting-balloon catheter;
    an integrated unit comprising an OCT sensor and an IVUS sensor located next to the expandable balloon for image monitoring; and
    a drive unit that advances or withdraws the cutting-balloon catheter and simultaneously rotating the OCT sensor and the IVUS sensor;
    an OCT signal lead and an IVUS signal lead that connect the OCT sensor and the IVUS sensor to the drive unit respectively; and a flexible drive shaft in which are the OCT signal lead and the IVUS signal lead, wherein the flexible drive shaft does not rotate and only the OCT sensor and the IVUS sensor rotate to avoid a friction between the cutting-balloon catheter and a vessel wall of the patient.

15. The x-ray apparatus as claimed in claim 14, further comprising an image correcting unit that corrects an image artifact of the x-ray image data due to the stent.

16. The x-ray apparatus as claimed in claim 14, further comprising a position sensor or an ECG sensor or combinations thereof.

17. The x-ray apparatus as claimed in claim 16, wherein the image data recorded by the x-ray apparatus and data recorded by the sensors are read out in a time sequence.

18. The x-ray apparatus as claimed in claim 16, wherein the x-ray image data recorded by the x-ray apparatus is combined or overlaid with an image data recorded by the IVUS sensor or the OCT sensor.

19. A method for performing a cutting-balloon intervention on a patient, comprising:

arranging a cutting-balloon catheter with an expandable balloon comprising an axially arranged knive;

pre-mounting a stent to the cutting-balloon catheter;

performing the cutting-balloon intervention on the patient using the cutting-balloon catheter and monitoring the intervention by an integrated unit comprising an OCT sensor and an IVUS sensor located next to the expandable balloon;

advancing or withdrawing the cutting-balloon catheter and simultaneously rotating the OCT sensor and the IVUS sensor by a drive unit;

connecting the OCT sensor and the IVUS sensor to the drive unit by an OCT signal lead and an IVUS signal lead respectively;

integrating the OCT signal lead and the IVUS signal lead inside a flexible drive shaft; and rotating only the OCT sensor and the IVUS sensor without rotating the flexible drive shaft to avoid a friction between the cutting-balloon catheter and a vessel wall of the patient.

\* \* \* \* \*